US00PP35638P2

(12) United States Plant Patent
Buckner

(10) Patent No.: US PP35,638 P2
(45) Date of Patent: Feb. 6, 2024

(54) ***HYDRANGEA* PLANT NAMED 'MDBPV1'**

(50) Latin Name: *Hydrangea paniculata*
Varietal Denomination: MDBPV1

(71) Applicant: Murray Buckner, Charlottesville, VA (US)

(72) Inventor: Murray Buckner, Charlottesville, VA (US)

( * ) Notice: Subject to any disclaimer, the term of this patent is extended or adjusted under 35 U.S.C. 154(b) by 0 days.

(21) Appl. No.: 18/109,657

(22) Filed: Feb. 14, 2023

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
CPC ..... A01H 5/02; A01H 5/00; A01H 6/48
See application file for complete search history.

*Primary Examiner* — June Hwu
(74) *Attorney, Agent, or Firm* — Cassandra Bright

(57) ABSTRACT

A new and distinct cultivar of *Hydrangea* plant named 'MDBPV1' is disclosed, characterized unique sepal coloration of a creamy white to white background with very distinctive pink veins. Fertile flowers open white with purple coloration. The new variety is a *Hydrangea*, typically produced as an outdoor ornamental plant.

3 Drawing Sheets

Latin name of the genus and species: *Hydrangea paniculata.*

Variety denomination: 'MDBPV1'.

BACKGROUND OF THE INVENTION

The new cultivar is a product of a planned breeding program conducted by the inventor at a commercial nursery in Palmyra, VA. The objective of the breeding program was to produce new *Hydrangea* varieties with unique sepal coloration. The open-pollination resulting in the new variety was made during 2020.

The seed parent is an unnamed, unpatented variety of *Hydrangea paniculata*. The pollen parent cannot be identified as this new selection resulted from an open-pollination.

The new variety was found and selected by the inventor in September of 2021 at the same nursery in Palmyra, VA. Asexual reproduction of the new cultivar 'MDBPV1' was first performed during January 2022 in Palmyra, VA, by hardwood cuttings. The new variety has also been propagated by softwood cuttings. Subsequent propagation has shown that the unique features of this cultivar are stable and reproduced true to type.

No plants of the new variety have been sold or otherwise made available to third parties at the time of this filing.

SUMMARY OF THE INVENTION

The cultivar 'MDBPV1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MDBPV1'. These characteristics in combination distinguish 'MDBPV1' as a new and distinct *Hydrangea* cultivar:

1. Unique sepal coloration; creamy white to white background with very distinctive pink veins.

2. Fertile flowers open white with purple coloration.
3. Greyed-Purple stems.
4. Large foliage.
5. Greyed-Red venation on both leaf surfaces.

PARENT COMPARISON

Plants of the new cultivar *Hydrangea* 'MDBPV1' are similar to plants of the seed parent in most horticultural characteristics, however, plants of 'MDBPV1' differ in the following:

1. Venation coloration in the new variety is darker and more prominent than in the seed parent.
2. The new variety produces inflorescences with more sepals.
3. Fertile flowers of the new variety are white with purple; fertile flowers of the seed parent are creamy white.
4. Flowers of the new variety are larger than flowers of the seed parent.

COMMERCIAL COMPARISON

Plants of the new cultivar *Hydrangea* 'MDBPV1' can be compared to the commercial variety *Hydrangea paniculata* 'White Moth', unpatented. Plants of 'MDBPV1' are similar to plants of 'White Moth' in most horticultural characteristics, however, plants of 'MDBPV1' differ in the following:

1. Sterile flower sepals of the new variety are cream to white with distinctive red-purple venation; sterile flower sepals of this comparator are pure white with no colored venation.
2. Fertile flowers of the new variety are bi-colored; fertile flowers of this comparator are solid white-green.

Plants of the new cultivar *Hydrangea* 'MDBPV1' can be compared to the commercial variety *Hydrangea paniculata* 'Unique', unpatented. Plants of 'MDBPV1' are similar to plants of 'Unique' in most horticultural characteristics, however, plants of 'MDBPV1' differ in the following:

1. Sterile flower sepals of the new variety are cream to white with distinctive red-purple venation; sterile flower sepals of this comparator are pure white, then fading to dusky pink with no colored venation.
2. Fertile flowers of the new variety are bi-colored; fertile flowers of this comparator are solid light yellow-green.

BRIEF DESCRIPTION OF THE PHOTOGRAPHS

The accompanying photograph in FIG. 1 illustrates in full color a typical plant of 'MDBPV1' grown outdoors in Palmyra, VA. This plant is approximately 1 year old, grown in a 2-gallon pot.

Figure 1:
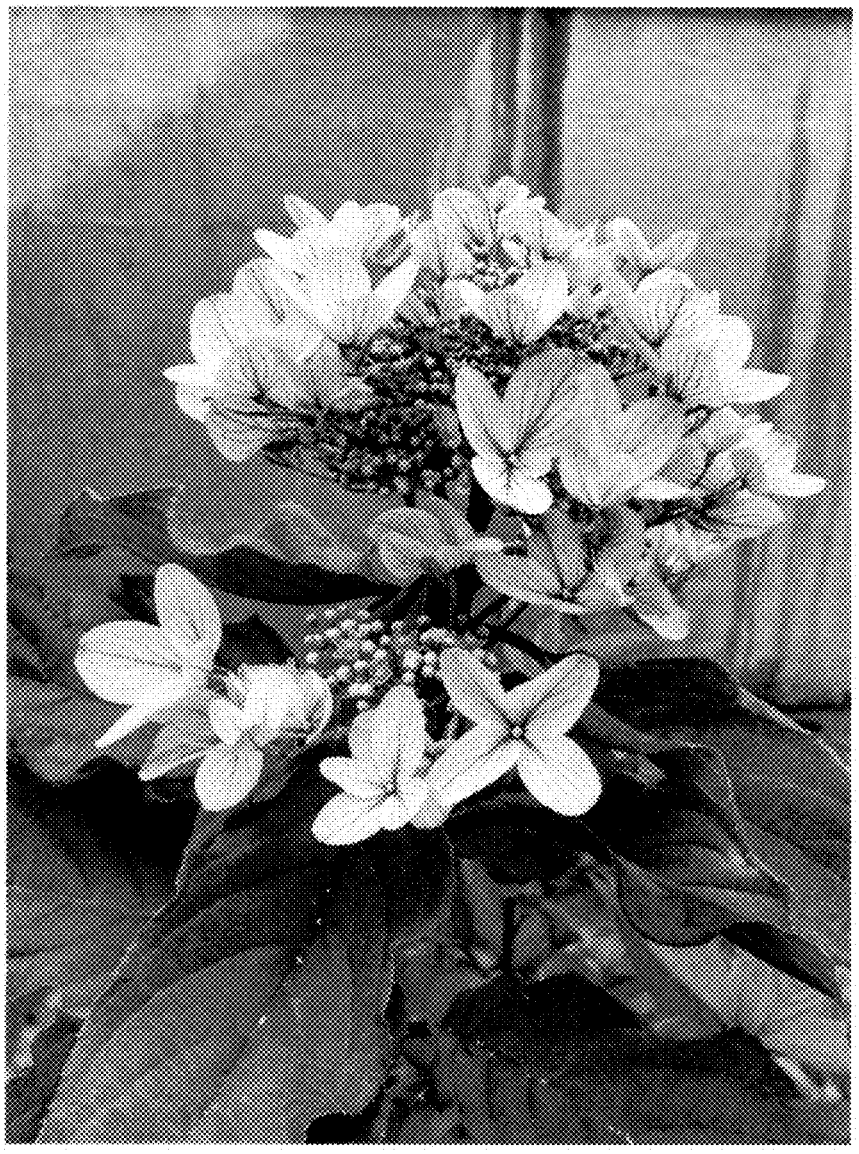
Figure 2:
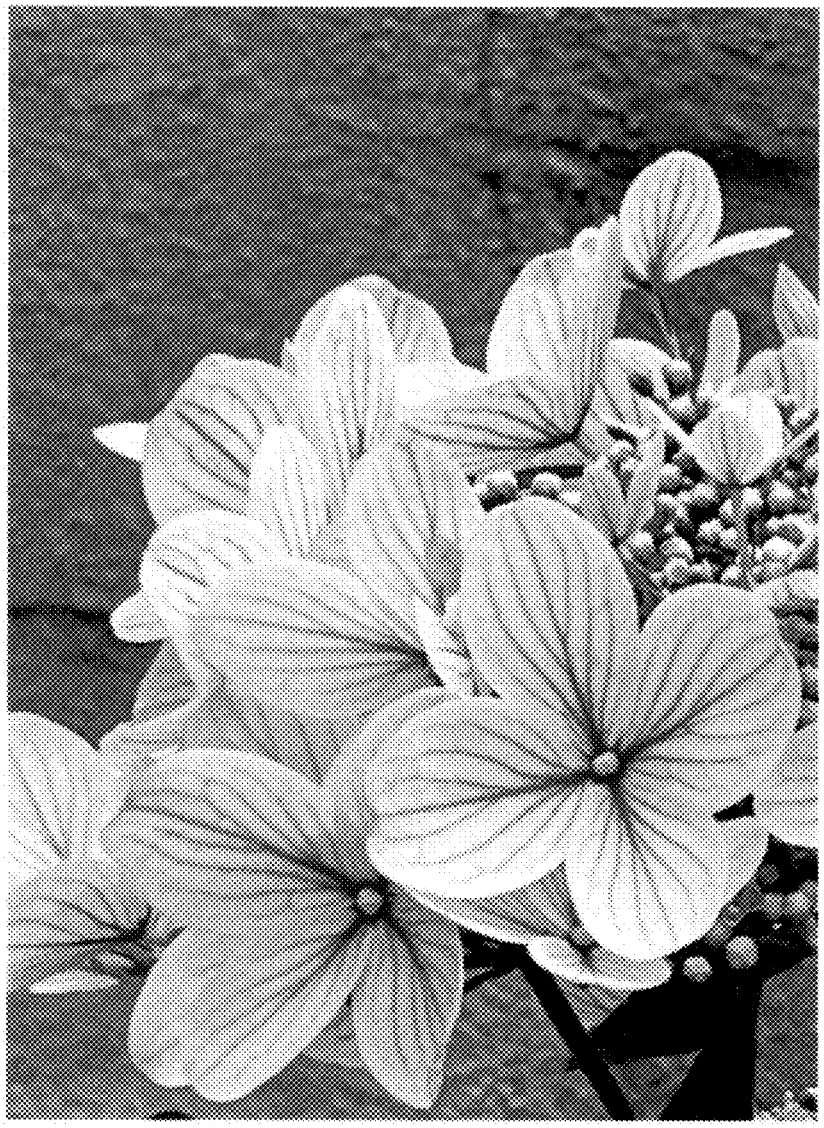
FIG. 2 illustrates in full color a close-up view of flowers of 'MDBPV1'.
Figure 3:
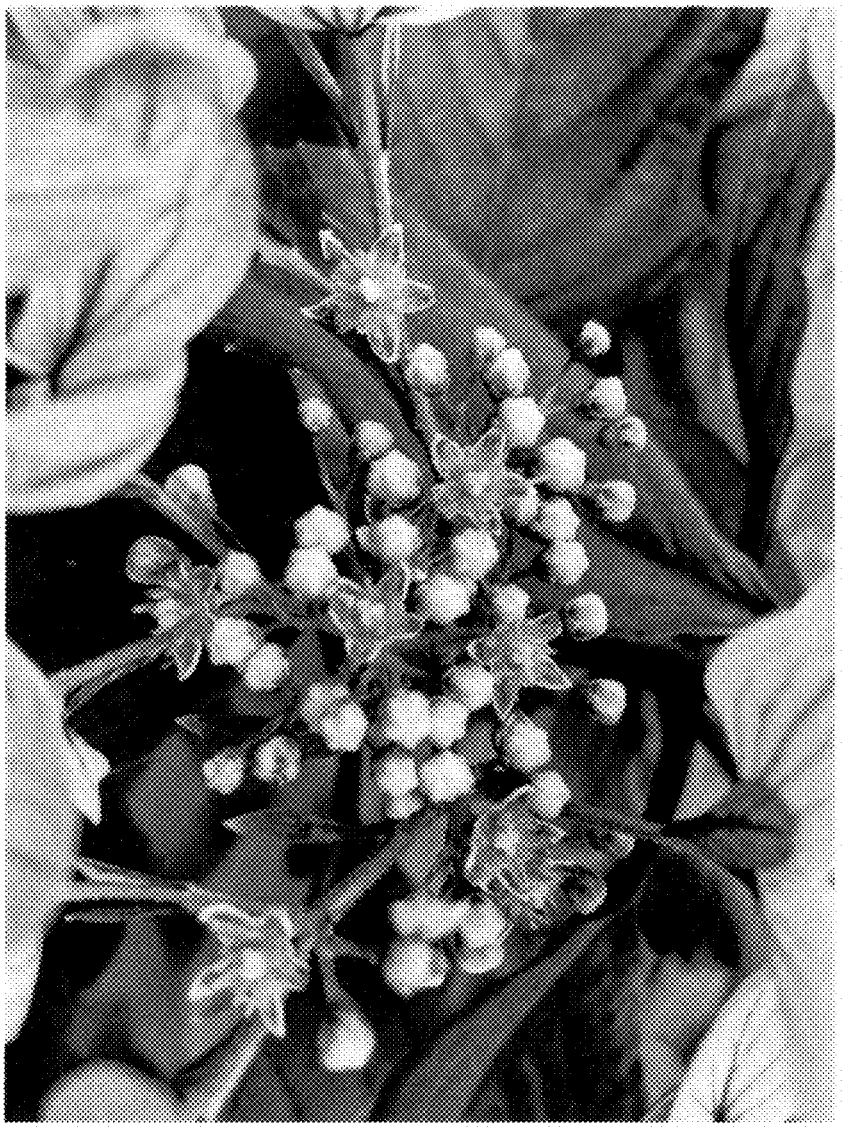
FIG. 3 is a close-up view of the fertile flowers of 'MDBPV1'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'MDBPV1' plants grown in outdoors in Palmyra, VA. The plants were about 2 years old. Temperatures ranged from about 3° C. to 12° C. at night to 18° C. to 30° C. during the day. No artificial light, photoperiodic treatments were given to the plants. Measurements and numerical values represent averages of typical plant types.

Botanical classification: *Hydrangea paniculata* 'MDBPV1'.

PROPAGATION

Typical method: Softwood cuttings.
Root initiation: 20 to 30 days at 20° C. during summer.
Time to produce rooted cutting: About 2 months at 20° C. during summer.
Roots: Dense, freely branching, fibrous, thick to thin. Creamy white to brown in color, not accurately measured with R.H.S. chart.

PLANT

Growth habit: Upright.
Height: About 150 cm.
Plant spread: About 100 cm.
Age of plant described: Approximately 2 years.
Plant vigor: Vigorous.
Stem:
- *Branching*.—Basal and lateral.
- *Number of main branches*.—10, depending on pruning.
- *Shape*.—Upright, somewhat V-shaped.
- *Color*.—RHS Greyed-Purple 183C.
- *Aspect*.—70 to 90°.
- *Strength*.—Quite strong.
- *Pubescence*.—None.
- *Internode length*.—Average 5.7 cm.

FOLIAGE

Leaf:
- *Arrangement*.—Whorl (3 leaves equally spaced around each node).
- *Shape*.—Ovate.
- *Length*.—Average 14 cm.
- *Width*.—Average 5 cm.
- *Apex*.—Acuminate.
- *Base*.—Obtuse.
- *Margin*.—Minutely serrate.
- *Aspect*. Undulate.
- *Texture of top surface*.—Roughly textured with coarse, bristly hairs.
- *Texture of bottom surface*.—Roughly textured with coarse, bristly hairs and pronounced venation.
- *Color*.—Young foliage upper side: RHS Green 143A. Young foliage under side: RHS Green 143B. Mature foliage upper side: RHS Green 137B. Mature foliage, under side: RHS Green 143A.

Venation:
- *Type*.—Pinnate.
- *Color*.—Upper side: RHS Yellow-Green N144A, central vein near petiole Greyed-Purple 183D. Under side: RHS Yellow-Green N144D with tinges of Greyed-Purple 183D close to petiole.

Petiole:
- *Length*.—Average 3.8 cm.
- *Width*.—Average 2.5 mm.
- *Color*.—Upper side: RHS Greyed-Purple 183D. Under side: RHS Greyed-Purple 183D.
- *Texture*.—Upper side: Lightly pubescent. Under side: Lightly pubescent.

INFLORESCENCE

Natural flowering season: Summer. July, August, September.
Inflorescence type: Lacecap.
Panicle:
- *Shape*.—Flattened, somewhat irregular hemispherical, or with more water, elongated.
- *Height*.—Average 22.9 cm.
- *Diameter*.—Average 17.8.

Sterile Flowers:
- *Flowers per inflorescence*.—Average 30.
- *Arrangement*.—Irregular whorls.
- *Aspect*.—Outward to slightly upright.
- *Shape*.—Cruciform
- *Diameter*.—5 cm.
- *Depth*.—2.8 cm.
- *Persistent or self-cleaning*.—Persistent.

Bud:
- *Length*.—9.5 mm.
- *Diameter*.—6.4 mm.
- *Shape*.—Orbicular.
- *Color*.—RHS Yellow-Green 150D.

Petals: No petals present.
Sepals:
- *Number*.—4.
- *Arrangement*.—Cruciform weakly overlapping.
- *Shape*.—Elliptic.
- *Tip*.—Rounded.
- *Base*.—Broad taper.
- *Margin*.—Entire.
- *Length*.—2.5 cm.

*Width.*—1.6 cm.
*Texture.*—Upper side: Glabrous. Under side: Glabrous.
*Color.*—When First Opening, Upper side: RHS Yellow 4C with distinctively strong venation near Red-Purple 61A. Faint apical flush near Greyed-Purple 185B. Basal flush near Red-Purple 60A. When First Opening, Under side: RHS Yellow 4C with distinctively strong venation near Red-Purple 61A flushed Greyed-Purple 185C. Faint apical flush near 185C. Faint basal flush near 60A. Semi-mature, Upper side: RHS Yellow-Green 150D with distinctively strong venation near Red-Purple 60B. Basal flush near Red-Purple 59C and 59D. Semi-mature, Under side: RHS Yellow-Green 150D with distinctively strong venation near Red-Purple 60B. Basal flush near Red-Purple 59C and 59D. Fully Opened, Upper side: RHS White N155C with distinctively strong venation near Red-Purple 60B flushed 59C. Basal flush near Red-Purple 59C and 59D. Fully Opened, Under side: White N155C with distinctively strong venation near Red-Purple 60B flushed 59C. Basal flush near Red-Purple 59C and 59D.

Pedicel:
*Length.*—About 1 cm.
*Diameter.*—About 3 mm
*Angle.*—Average 45°.
*Strength.*—Moderate.
*Texture.*—Smooth.
*Color.*—RHS Greyed-Purple 187B flushed Red-Purple 58A.

Fertile flowers:
*Flowers per inflorescence.*—Around 50 to 100.
*Aspect.*—Upright and outward.
*Shape.*—Stellate.
*Diameter.*—About 1 cm.
*Depth.*—About 8 mm.
*Persistent or self-cleaning.*—Self-cleaning.

Bud:
*Length.*—About 7 mm.
*Diameter.*—About 7 mm.
*Shape.*—Orbicular.
*Color.*—RHS White N155A flushed Greyed-Purple N187D.

Petals:
*Number per flower.*—5.
*Arrangement.*—Stellate.
*Shape.*—Narrowly elliptic.
*Tip.*—Acute.
*Base.*—Truncate.
*Margin.*—Entire.
*Length.*—About 6 mm.
*Width.*—About 2 mm.
*Texture.*—Upper side: Smooth. Under side: Smooth.
*Color.*—When Opening, Upper side: RHS White N155B, strong central streaks near Greyed-Purple N186B with Red-Purple 59A. When Opening, Under side: RHS White N155B, faint to moderate central streaks near Greyed-Purple N186B with Red-Purple 59A. Fully Opened, Upper side: RHS White N155B, strong central streaks near Greyed-Purple N186B with Red-Purple 59A. Fully Opened, Under side: RHS White N155B, moderate central streaks near Greyed-Purple N186B with Red-Purple 59A.

Calyx/sepal: Calyx present. About 4 mm in length and 3 mm in diameter. Colored near Greyed-Purple N186B streaked White N155B. Individual sepals fused approximately 80% of length, acute at apex.

Pedicel:
*Length.*—Average range 5 mm to 9 mm.
*Diameter.*—1 mm.
*Angle.*—90°.
*Strength.*—Moderate.
*Texture.*—Glabrous.
*Color.*—RHS White N155C flushed Greyed-Purple N186B.

REPRODUCTIVE ORGANS

Sterile flower: Central, globular structure with no definable parts.

Fertile flower:

Stamen:
*Number.*—9 to 12 mm.
*Filament length.*—5 to 8 mm.
*Filament color.*—RHS White 155D Anther:
*Shape.*—Rounded, basifixed.
*Length.*—About 1 mm.
*Color.*—RHS Yellow-White 158A.
*Pollen amount.*—Scant to none.
*Pollen color.*—RHS Yellow-White 158D.

Pistil:
*Number.*—1.
*Length.*—4 mm.

Stigma:
*Shape.*—3-parted.
*Color.*—RHS Green-White 157D.
*Style length.*—3 mm.
*Style color*. RHS Green-White 157D.
*Ovary color.*—RHS Green-White 157D.

OTHER CHARACTERISTICS

Disease resistance: Neither resistance nor susceptibility to the normal diseases and pests of *Hydrangea* has been observed.

Drought tolerance and cold tolerance: The new cultivar can tolerate cold temperatures to approximately −31° C. and tolerates an upper temperature range to at least 38° C. No tolerance for drought.

Fruit/seed production: Dry, cup-shaped fruit colored near Greyed-Green 191C flushed Greyed-Purple N187B, about 5 mm in diameter and length. Moderate quantity of seeds produced, flat, colored near Grey-Brown N199B, about 1 mm in width and 2 mm in length.

What is claimed is:

1. A new and distinct cultivar of *Hydrangea* plant named 'MDBPV1' as herein illustrated and described.

* * * * *